(12) United States Patent
Takeuchi et al.

(10) Patent No.: US 6,892,142 B2
(45) Date of Patent: May 10, 2005

(54) METHOD OF ANALYZING PARTICLES SUSPENDED IN LIQUID AND LIQUID-SUSPENDED PARTICLE ANALYZER FOR CARRYING OUT THE METHOD

(75) Inventors: Kazuo Takeuchi, Wako (JP); Kikuo Okuyama, Wako (JP); Wuled Lenggoro, Wako (JP)

(73) Assignee: Riken, Wako (JP)

( * ) Notice: Subject to any disclaimer, the term of this patent is extended or adjusted under 35 U.S.C. 154(b) by 78 days.

(21) Appl. No.: 10/294,747

(22) Filed: Nov. 15, 2002

(65) Prior Publication Data

US 2003/0093228 A1 May 15, 2003

(30) Foreign Application Priority Data

Nov. 15, 2001 (JP) ........................ 2001-349667

(51) Int. Cl.⁷ .................. G01N 31/00; G01N 11/00
(52) U.S. Cl. .................................. 702/23; 73/53.01
(58) Field of Search ........................ 702/23, 26, 29; 73/1.02, 1.05, 53.01, 865.5

(56) References Cited

U.S. PATENT DOCUMENTS

| 4,284,496 A |   | 8/1981  | Newton           |        |
|-------------|---|---------|------------------|--------|
| 4,670,137 A |   | 6/1987  | Koseki et al.    |        |
| 4,736,311 A | * | 4/1988  | Takeuchi et al.  | 702/29 |
| 4,761,074 A |   | 8/1988  | Kohsaka et al.   |        |
| 4,790,650 A | * | 12/1988 | Keady            | 356/37 |
| 4,794,086 A |   | 12/1988 | Kasper et al.    |        |
| 4,894,529 A |   | 1/1990  | Borden et al.    |        |
| 5,076,097 A | * | 12/1991 | Zarrin et al.    | 73/61.72 |
| 5,095,451 A | * | 3/1992  | Allen            | 702/29 |
| 5,247,842 A | * | 9/1993  | Kaufman et al.   | 73/865.5 |

(Continued)

FOREIGN PATENT DOCUMENTS

| JP | 62-222145 A   | 9/1987  |
|----|---------------|---------|
| JP | 6-12941 U     | 2/1994  |
| JP | 10-288609 A   | 10/1998 |
| JP | 11-264790 A   | 9/1999  |
| JP | 2000-2722 A   | 1/2000  |
| JP | 2000-002722 A | 1/2000  |
| JP | 2000-46720 A  | 2/2000  |
| JP | 2000-046720 A | 2/2000  |

OTHER PUBLICATIONS

Kaufman, Analysis of Biomolecules Using Electrospray and Nanoparticle Methods: The Gas–Phase Electrophoretic Mobility Molecular Analyzer (GEMMA), 1998, J. Aerosol Sci., vol. 29, No. 5/6, pp 537–552.*

(Continued)

Primary Examiner—John Barlow
Assistant Examiner—Toan M. Le
(74) Attorney, Agent, or Firm—Birch Stewart Kolasch & Birch, LLP

(57) ABSTRACT

A liquid-suspended particle analyzer includes: a fine liquid droplet producing device for atomizing a liquid pumped from a sample container by a fixed-displacement pump to produce fine liquid droplets suspended in a carrier gas; an evaporator for evaporating the liquid parts of the fine liquid droplets to produce an aerosol of the carrier gas and particles suspended in the carrier gas; a differential mobility classifier for classifying the particles of the aerosol by particle size according to mobility; and a Faraday cup electrometer for counting the respective numbers of the particles of the particle groups classified by particle size by the differential mobility classifier so as to determine the respective particle concentrations of the groups. The fine liquid droplets producing device includes an electrospraying device adapted to convert the liquid supplied by the liquid supply device into charged fine liquid droplets; and an atomizer adapted to suspend the charged fine liquid droplets produced by the electrospraying device in the carrier gas.

10 Claims, 3 Drawing Sheets

U.S. PATENT DOCUMENTS

| | | | | |
|---|---|---|---|---|
| 5,532,943 | A | * 7/1996 | Asano et al. | 702/21 |
| 5,922,976 | A | * 7/1999 | Russell et al. | 73/865.5 |
| 5,992,244 | A | 11/1999 | Pui et al. | |
| 6,230,572 | B1 | * 5/2001 | Pui et al. | 73/863.21 |
| 6,259,101 | B1 | * 7/2001 | Wexler et al. | 250/423 P |
| 6,263,744 | B1 | * 7/2001 | Russell et al. | 73/865.5 |
| 6,491,872 | B1 | * 12/2002 | Wick | 422/72 |
| 6,553,849 | B1 | * 4/2003 | Scofield et al. | 73/865.5 |
| 6,662,117 | B2 | * 12/2003 | Naito | 702/29 |
| 6,674,528 | B2 | * 1/2004 | Adachi et al. | 356/336 |

OTHER PUBLICATIONS

Mouradian et al., DNA Analysis Using an Electorspray Scanning Mobility Particle Sizer, 1997, Anal. Chem., vol. 69, pp 919–925.*

Kaufman et al., Macromolecule Analysis Based on Electrophoretic Mobility in Air: Globular Proteins, 1996, Anal. Chem., vol. 68, No. 11, pp 1895–1904.*

Seto et al., Size Distribution Measurement of Nanometer–Sized Aerosol Particle Using DMA Under Low–Pressure Conditions, 1997, Journal Aerosol Science, vol. 28, No. 2, pp. 193–206.*

Alonso et al., Simplified Analysis of the Effect of Brownian Diffusion on the Relationship Between Applied Voltage and Central Mobility in the DMA, 1998, Journal Aerosol Science, vol. 29, No. 8, pp. 985–994.*

Bruins, Mechanistic Aspects of electrospray Ionization, 1998, Journal of Chromatography A, 794, pp. 345–357.*

Journal of Electrostatics, Elsevier Science Publishers B.V. Amsterdam, NL, vol. 51–52, May 2001, pp. 193–199, XP004341069, "Smoke precipitation by charged water aerosol," Balachandran et al.

Industry Applications Conf., 1996, $31^{st}$ IAS Annual Mtg., IAS '96, Conf. Record of the 1996 IEEE, San Diego, CA, Oct. 6–10, 1996, pp. 1789–1794 (*pp. 1791–1739), Oct. 6, 1996, XP010201257, "Precipitation of inhalable smoke particles etc.," Balachandran et al.

Chemical Physics Letters, Oct. 13, 2000, Elsevier, NL, vol. 329, No. 1–2, pp. 52–60 (*pp. 52–54), XP002232537, "FTIR investigation of 1–9 non–volatile molecular nanoparticles," Signorell et al.

* cited by examiner

METHOD OF ANALYZING PARTICLES SUSPENDED IN LIQUID AND LIQUID-SUSPENDED PARTICLE ANALYZER FOR CARRYING OUT THE METHOD

This nonprovisional application claims priority under 35 U.S.C. § 119(a) on Patent Application No. 2001-349667 filed in JAPAN on Nov. 15, 2001, which is herein incorporated by reference.

BACKGROUND OF THE INVENTION

1. Field of the Invention

The present invention relates to a method of analyzing particles suspended in a liquid, and a liquid-suspended particle analyzer for carrying out the method. More particularly, the present invention relates to a method capable of accurately measuring the particle size of particles having sizes on the order of nanometers (hereinafter, referred to as "nanoparticles") suspended in a liquid and of determining the particle size distribution of the nanoparticles in a short time, and a liquid-suspended particle analyzer for carrying out the method.

2. Description of the Related Art

In a semiconductor device fabricating process for instance, a silicon wafer is cleaned with cleaning water, such as ultrapure water, to remove contaminants from the surfaces of the silicon wafer. If the cleaning water contains particles, the particles contained in the cleaning water remain and adhere to the surfaces of the silicon wafer after cleaning and drying operations. Such particles cause detrimental effects on the formation of an integrated circuit on the surface of the silicon wafer and reduce the yield of semiconductor devices.

In precision machine manufacturing processes, workpieces are cleaned with a volatile solvent to remove anticorrosive oil coating the workpieces and cutting fluids flowed over the workpiece in machining. If the volatile solvent contains hard particles, such as fine grains of sand and fine fragments of cutting tools, precision-machine parts are contaminated with those hard particles, and precision machines are constructed by assembling such precision-machine parts contaminated with hard particles. When a precision machine thus assembled is operated, the particles adhering to sliding surfaces cause abnormal abrasion and, consequently, the precision machine unable to function properly.

To avoid such problems and to improve the yield and the reliability of products, the cleanliness of the liquid, such as the cleaning water and the volatile solvent, must be monitored and proper measures must be taken to prevent contamination with particles.

Optical methods, such as light scattering methods and light transmission methods, and microscopic methods that analyzes an image formed by an electron beam microscope have been generally used for measuring the particle size and number of particles suspended in liquids, such as cleaning water and volatile solvents, to monitor the cleanliness of the liquids.

Optical methods, such as light scattering methods and light transmission methods, are subject to restrictions on the measurable particle size of particles. Even an optical particle size measuring instrument having the highest sensitivity is capable of measuring particle sizes on the order of submicrometers and incapable of measuring particle sizes below submicrometers. Microscopic methods that analyze an image formed by an electron beam microscope require advanced techniques and need a long time for image analysis.

SUMMARY OF THE INVENTION

The present invention has been made in view of those problems and it is therefore an object of the present invention to provide a method of analyzing particles, such as nanoparticles, suspended in a liquid, and a comparatively inexpensive liquid-suspended particle analyzer for carrying out the method, capable of being easily operated, of accurately measuring the particle size of particles in a short time and determining a particle size distribution.

According to a first aspect of the present invention, a liquid-suspended particle analyzer for analyzing particles suspended in a liquid comprises: a liquid supply device that supplies a liquid to be analyzed; a fine liquid droplet producing device that produces fine liquid droplets suspended in a carrier gas by atomizing the liquid supplied by the liquid supply device; an evaporator that produces an aerosol of the carrier gas and particles suspended in the carrier gas by evaporating the liquid parts of the fine liquid droplets produced by the fine liquid droplet producing device; a classifier that classifies the particles of the aerosol produced by the evaporator into particle groups by particle size; and a particle analyzer that analyzes the particle groups of the particles classified by particle size by the classifier.

In the liquid-suspended particle analyzer according to the first aspect of the present invention, it is preferable that the fine liquid droplet producing device includes an electrospraying device adapted to convert the liquid supplied by the liquid supply device into charged fine liquid droplets, and an atomizer adapted to suspend the charged fine liquid droplets produced by the electrospraying device in the carrier gas. Preferably, the atomizer is provided with a radiation source capable of charging the charged fine liquid droplets produced by the electrospraying device in the Boltzmann equilibrium charge distribution. Preferably, an ammeter is connected to the atomizer to measure a quantity of charge discharged from the fine liquid droplets collided against an inner wall of the atomizer.

In the liquid-suspended particle analyzer according to the first aspect of the present invention, it is preferable that the classifier is a differential mobility classifier adapted to classify the particles of the aerosol produced by the evaporator according to mobility.

In the liquid-suspended particle analyzer according to the first aspect of the present invention, it is preferable that the particle analyzer is a particle counter adapted to count the respective numbers of the particles of the particle groups classified by the classifier. It is preferable that the particle counter is one selected from a group consisting of a Faraday cup electrometer, an ion counter and a nuclear condensation counter.

According to a second aspect of the present invention, a liquid-suspended particle analyzing method of analyzing particles suspended in a liquid comprises the steps of: producing fine liquid droplets suspended in a carrier gas by atomizing a liquid to be analyzed; producing an aerosol of the carrier gas and particles suspended in the carrier gas by evaporating the liquid parts of the fine liquid droplets; classifying the particles of the aerosol into particle groups by particle size; and analyzing the particle groups of the particles classified by particle size.

In the liquid-suspended particle analyzing method according to the second aspect of the present invention, it is preferable that, in the step of analyzing the particles of the particle groups, respective numbers of the particles of the particle groups classified by particle size are counted so that a particle size distribution of the particles suspended in the liquid is determined on the basis of the counted numbers of the particles.

According to the present invention, the liquid suspending the particles is atomized into fine liquid droplets suspended in the carrier gas, and the liquid parts of the fine liquid droplets is evaporated to produce the aerosol of the carrier gas and the particles suspended in the carrier gas. Therefore, the particles of optional particle sizes including nanoparticles and suspended in the liquid can be suspended in the carrier gas such that the particles do not aggregate. The particles thus suspended in the carrier gas can be classified by particle size by the classifier and the groups of the particles can be analyzed. Thus, the particle size distribution and such of the particles, such as nanoparticles, can be accurately measured in a short time.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

Figure 1:
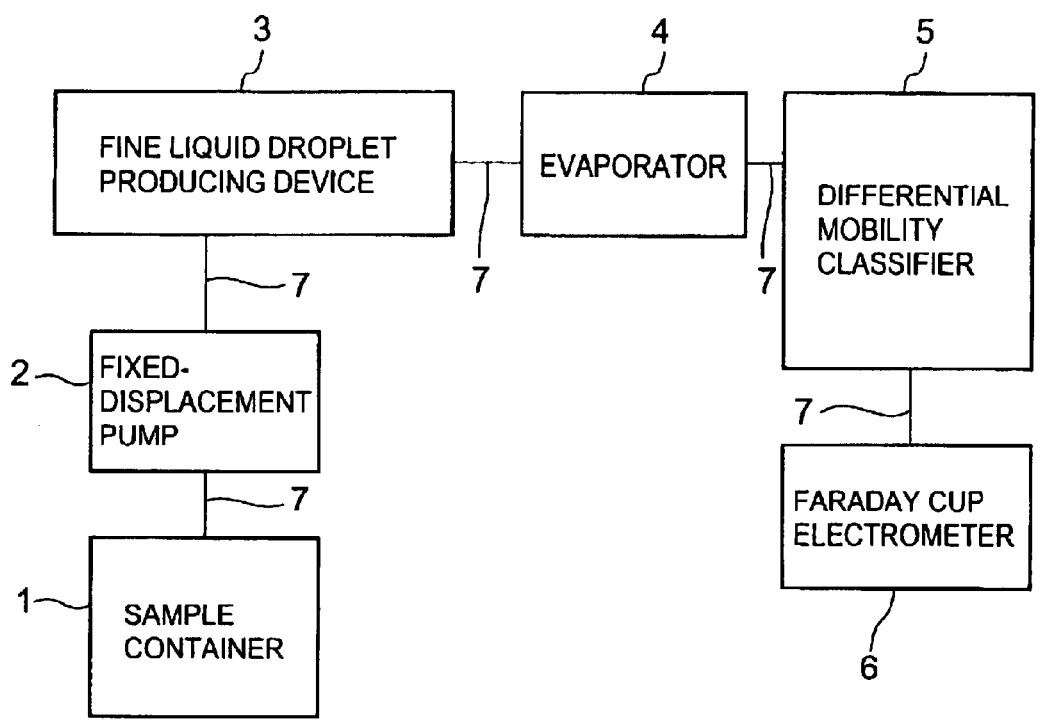
FIG. 1 is a block diagram of a liquid-suspended particle analyzer in a preferred embodiment of the present invention.

Referring to FIG. 1, a liquid-suspended particle analyzer in a preferred embodiment of the present invention analyzes particles suspended in a liquid. The liquid-suspended particle analyzer includes a liquid supply device comprised of a sample container 1, i.e., a liquid source, containing a liquid to be analyzed, and a fixed-displacement pump 2. The liquid-suspended particle analyzer further includes: a fine liquid droplet producing device 3 that produces fine liquid droplets suspended in a carrier gas by atomizing the liquid pumped by the fixed-displacement pump 2 from the sample container 1; an evaporator 4 that produces an aerosol of the carrier gas and particles suspended in the carrier gas by evaporating the liquid parts of the fine liquid droplets produced by the fine liquid droplet producing device 3; a differential mobility classifier 5 that classifies the particles of the aerosol produced by the evaporator 4 into particle groups by particle size according to mobility, and a Faraday cup electrometer (particle counter) 6 that counts the respective numbers of the particles of the particle groups classified by particle size by the differential mobility classifier 5. The sample container 1, the fixed-displacement pump 2, the fine liquid droplet producing device 3, the evaporator 4, the differential mobility classifier 5 and the Faraday cup electrometer 6 are connected properly by pipes 7.

The fine liquid droplet producing device 3, the evaporator 4, the differential mobility classifier 5 and the Faraday cup electrometer 6 of the liquid-suspended particle analyzer shown in FIG. 1 will be described with reference to FIGS. 2 to 6.

Figure 2:
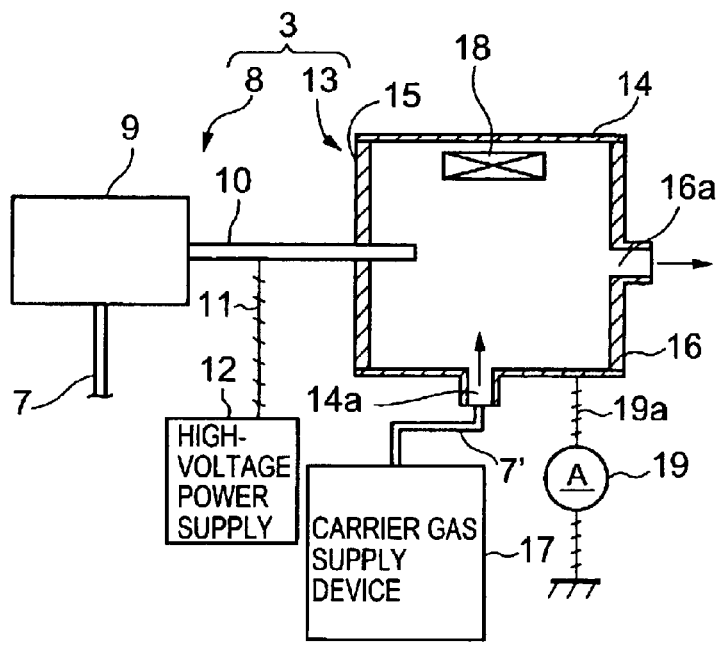
FIG. 2 is a schematic view of a fine liquid droplet producing device included in the liquid-suspended particle analyzer shown in FIG. 1.
Figure 3:
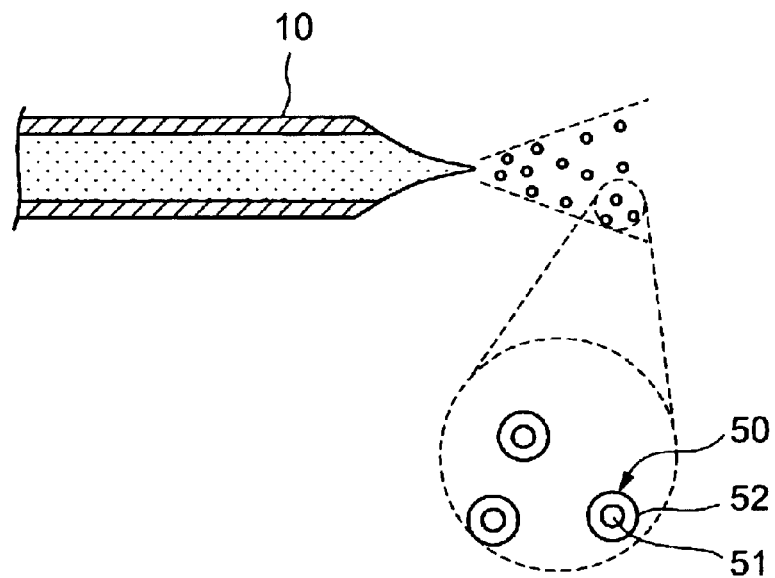
FIG. 3 is a typical view of assistance in explaining a process of producing fine liquid droplets by an electrospraying device included in the fine liquid droplet producing device shown in FIG. 2.

Referring to FIG. 2, the fine liquid droplet producing device 3 has an electrospraying device 8 that produces charged fine liquid droplets, and an atomizer 13 that atomizes the charged fine liquid droplets produced by the electrospraying device 8 in a carrier gas. The electrospraying device 8 has a body 9 for receiving the liquid pumped by the fixed-displacement pump 2 from the sample container 1 through the pipe 7, and a nozzle 10 for spraying the liquid supplied thereto from the body 9 for atomization. The body 9 is formed of an insulating material, and the nozzle 10 is formed of a conductive material. A high-voltage power supply 12 is connected to the nozzle 10 by a line 11 to apply a high voltage in the range of about 1 to about 5 kV DC to the nozzle 10 for charging the liquid supplied to the nozzle 10. The nozzle 10 has a front end part inserted in the atomizer 13. The liquid is sprayed by the nozzle 10 into the atomizer 13 to produce fine liquid droplets 50 of the liquid 52 including particles 51 as shown in FIG. 3. Preferably, the fine liquid droplets 50 thus produced have sizes, for example, in the range of about 5 to about 100 nm so that each of the fine liquid droplets contains one particle. The sizes of the fine liquid droplets can be properly determined by selectively determining the size of the nozzle 10, the flow rate of the liquid in the nozzle 10, and the voltage applied to the nozzle 10.

The atomizer 13 has a cylindrical vessel 14, an entrance end wall 15 attached to one end of the cylindrical vessel 14, and an exit end wall 16 attached to the other end of the cylindrical vessel 14. The entrance end wall 15 is formed of an insulating material. The front end part of the nozzle 10 of the electrospraying device 8 is inserted through a central part of the entrance end wall 15 in the atomizer 13. A carrier gas inlet 14a is formed in the cylindrical vessel 14, and a carrier gas supply device 17 is connected to the carrier gas inlet 14a by a pipe 7' to supply a carrier gas, such as nitrogen gas, into the atomizer 13. Thus, charged fine liquid droplets produced in the atomizer 13 are suspended in the carrier gas. An outlet 16a is formed in the exit end wall 16 to discharge the carrier gas suspending the charged fine liquid droplets into the evaporator 4. Preferably, the temperature of the atmosphere in the atomizer 13 is on the order of a room temperature, and the pressure of the same is on the order of the atmospheric pressure. Preferably, the carrier gas is supplied into the atomizer 13 at a flow rate in the range of about 0.5 to about 5 l/min. The cylindrical vessel 14 and the exit end wall 16 are formed of a conductive material.

A radiation source 18, such as a radioactive isotope of americium, is placed in the atomizer 13 to charge the charged fine liquid droplets produced by the electrospraying device 8 provided with the nozzle 10 in the Boltzmann equilibrium charge distribution. A conductor 19a connects the cylindrical vessel 14 of the atomizer 13 to the ground. An ammeter 19 is inserted in the conductor 19a.

Figure 4:
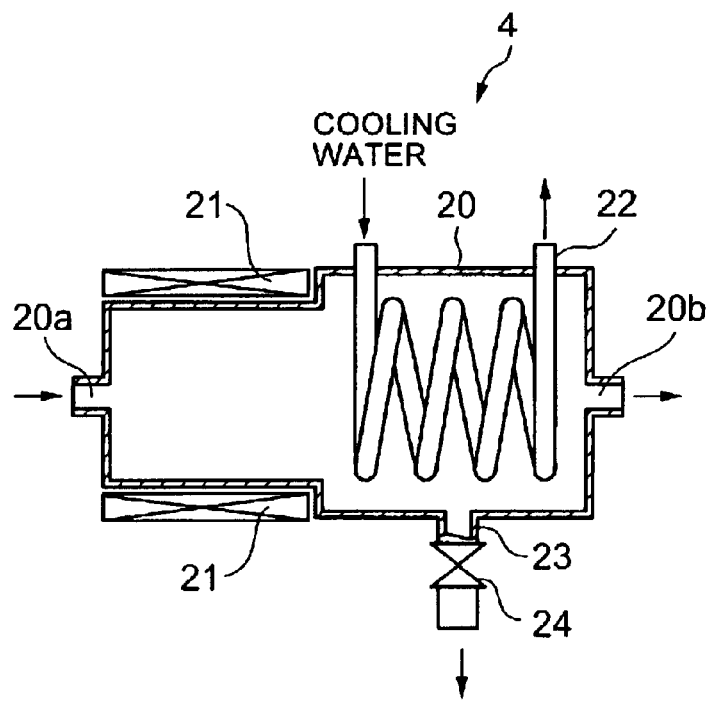
FIG. 4 is a schematic sectional view of an evaporator included in the liquid-suspended particle analyzer shown in FIG. 1.

Referring to FIG. 4, the evaporator 4 has a cylindrical vessel 20 having opposite ends closed by end walls. One of the end walls is provided with an inlet 20a to let the charged fine liquid droplets suspended in the carrier gas and produced by the atomizer 13 of the fine liquid droplet producing device 3 flow into the cylindrical vessel 20, and the other end wall is provided with an outlet 20b to let the aerosol of the carrier gas and the particles suspended in the carrier gas by evaporating the liquid parts of the charged fine liquid droplets produced by the fine liquid droplet producing device 3 flow into the differential mobility classifier 5. A heater 21 is combined with an upstream end part of the side wall of the cylindrical vessel 20 of the evaporator 4 to evaporate the liquid parts of the charged fine liquid droplets produced by the fine liquid droplet producing device 3. A cooling device 22 is disposed in a downstream part of the cylindrical vessel 20 to condense the evaporated liquid parts for recovery. A drain pipe 23 provided with a shut-off valve 24 is connected to a downstream part of the sidewall of the cylindrical vessel 20. Preferably, the heater 21 heats the charged fine liquid droplets at a heating temperature in the range of a room temperature to about 100° C., and the cooling device 22 cools the evaporated liquid parts at a cooling temperature in the range of about 10 to about 15° C. The heating temperature and the cooling temperature may be regulated by temperature regulating means.

Figure 5:
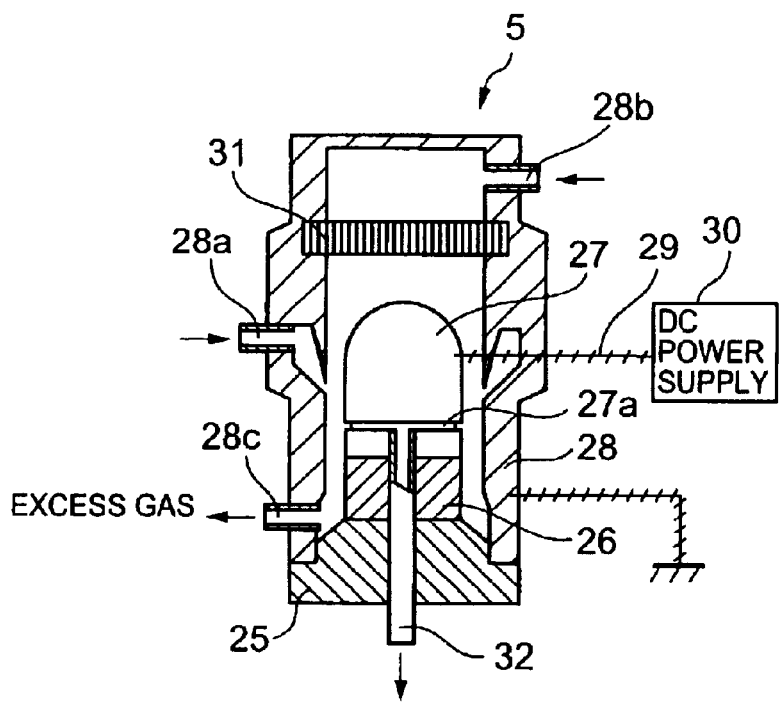
FIG. 5 is a schematic sectional view of a differential mobility classifier included in the liquid-suspended particle analyzer shown in FIG. 1.

Referring to FIG. 5, the differential mobility classifier 5 has a base 25, a center rod 27 connected to the base 25 by an annular insulator 26, and a case 28 connected to the base 25 so as to surround the center rod 27. The center rod 27 is provided with an annular slit 27a to discharge classified charged particles through a particle discharge pipe 32. The case 28 is provided with an annular aerosol inlet 28a to let the aerosol of the carrier gas and the charged particles produced by the evaporator 4 into the case 28. The case 28 is provided in its upper part with a sheath gas inlet 28b. A straightening mesh 31 is disposed in an upper part of the interior of the case 28 to produce a laminar flow of the sheath gas. A sheath gas introduced through the sheath gas inlet 28b into the case 28 is discharged through an excess gas discharge port 28c formed in a lower part of the case 28 by a pump or the like, not shown. The center rod 27 and the case 28 are formed of conductive materials. A conductor 29 connects the center rod 27 to a DC power supply 30. The case 28 is connected to a ground by a conductor.

Parameters, including the flow rate of the sheath gas, the voltage to be applied to the center rod 27, and dimensions of the center rod 27 and the case 28, defining the functions of the differential mobility classifier 5 are determined properly according to the particle size of the particles to be classified, which is mentioned in JP-A Nos. 288609/1998, 264790/1999 and 46720/2000.

Figure 6:
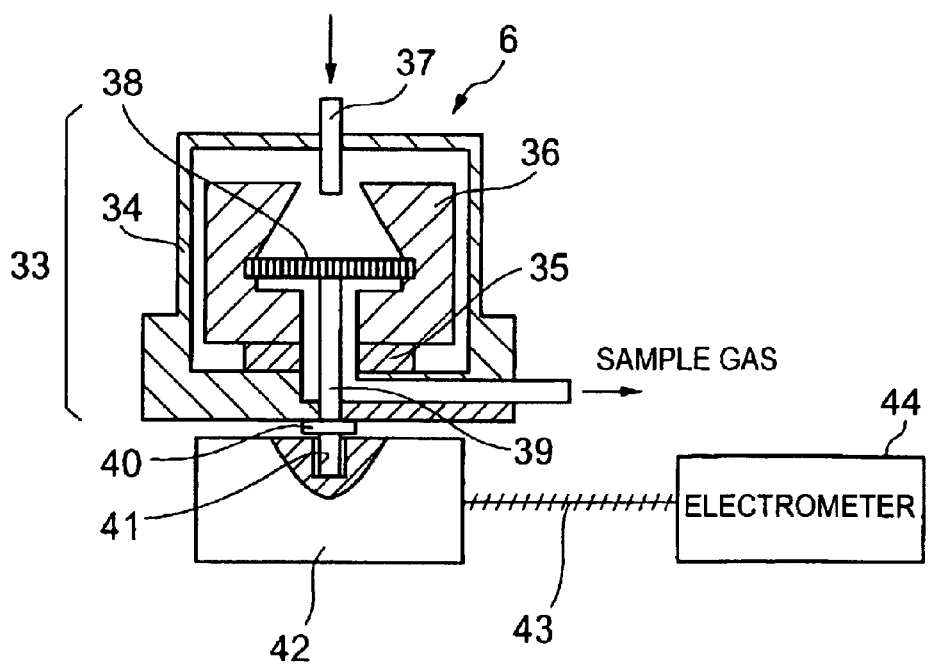
FIG. 6 is a schematic sectional view of a Faraday cup electrometer included in the liquid-suspended particle analyzer shown in FIG. 1.

Referring to FIG. 6, the Faraday cup electrometer 6 has a Faraday cup 33 to deposit charged particles classified by particle size by the differential mobility classifier 5, a preamplifier 42 for converting a weak current produced by the charge discharged from the charged particles deposited in the Faraday cup 33 into a corresponding voltage and amplifying the voltage, an electrometer 44 for converting the voltage amplified by the preamplifier 42 into the weak current produced in the Faraday cup 33. The Faraday cup 33 is a double-wall metal vessel consisting of an outer vessel 34, an inner vessel 36, and an annular insulator 35 connecting the inner vessel 36 to the outer vessel 34. A particle supply pipe 37 is connected to the outer vessel 34 to supply the charged particles classified by particle size by the differential mobility classifier 5 into the outer vessel 34. A conducting filter 38 is held in the inner vessel 36 to deposit the charged particles supplied into the inner vessel 36. A conductive rod 39 is attached to the lower surface of the conductive filter 38. A lower end part of the conductive rod 39 is screwed in a threaded hole formed in a receiving part 41 of the preamplifier 42 (JP-A No. 2722/2000). A fastening ring 40 is interposed between the outer vessel 34 of the Faraday cup 32 and the preamplifier 42. The preamplifier 42 and the electrometer 44 are connected by a double-shielded wire 43 for noise prevention.

The operation of the liquid-suspended particle analyzer thus constructed will be described. Referring to FIG. 1, a liquid to be analyzed contained in the sample container 1 is pumped through the pipe 7 into the fine liquid droplet producing device 3 by the fixed-displacement pump 2. Then, as shown in FIG. 2, the liquid supplied through the pipe 7 into the fine liquid droplet producing device 3 flows through the body 9 of the electrospraying device 8 to the nozzle 10 and is sprayed through the nozzle 10 into the atomizer 13. Consequently, fine liquid droplets 50 of the liquid 52 each including a particle 51 as shown in FIG. 3 are produced. The liquid supplied to the nozzle 10 is charged by applying a high voltage to the nozzle 10 by the high-voltage power supply 12. Upon the formation of the fine liquid droplets by spraying the liquid through the nozzle 10, the fine liquid droplets are exposed to α-rays emitted by the radiation source 18 and are charged in the Boltzmann equilibrium charge distribution. The charged fine liquid droplets produced in the atomizer 13 are suspended in the carrier gas supplied from the carrier gas supply device 17 through the carrier gas inlet 14a into the cylindrical vessel 14. The carrier gas suspending the charged fine liquid droplets flows through the outlet 16a of the exit end wall 16 to the evaporator 4.

Referring to FIG. 4, the charged fine liquid droplets discharged from the atomizer 13 of the fine liquid droplet producing device 3 flows through the inlet 20a into the cylindrical vessel 20. The heater 21 disposed at the upstream part of the cylindrical vessel 20 heats the charged fine liquid droplets to evaporate the liquid parts of the charged fine liquid droplets. Consequently, an aerosol of the carrier gas and the charged particles is produced. The aerosol flows through the outlet 20b of the cylindrical vessel 20 toward the differential mobility classifier 5. The vapor of the liquid produced by heating the liquid parts of the charged fine liquid droplets by the heater 21 is condensed in the liquid by cooling the same by the cooling device 22 disposed in the downstream part of the cylindrical vessel 20, and the liquid is drained from the cylindrical vessel 20 through the drain pipe 23.

The aerosol of the carrier gas and the charged particles is classified by particle size by the differential mobility classifier 5 shown in FIG. 5. The aerosol discharged from the evaporator 4 flows through the aerosol inlet 28a of the case 28 into a space extending between the center rod 27 and the case 28. Since the sheath gas supplied through the sheath gas inlet 28b of the case 28 and straightened by the straightening mesh 31 flows down in a laminar flow, only charged particles of a specific particle size among those included in the aerosol supplied through the aerosol inlet 28a are drawn through the annular slit 27a of the center rod 27 into the particle discharge pipe 32 and are discharged toward the Faraday cup electrometer 6. The particle size of the charged particles to be thus collected is dependent mainly on the flow rate of the sheath gas and the voltage applied to the center rod 27.

The particle concentrations, i.e., the numbers of particles per unit volume, of the charged particles respectively included in groups of the charged particles respectively having different particle sizes classified by the differential mobility classifier 5 are measured by the Faraday cup electrometer 6 shown in FIG. 6. More concretely, the charged particles of each group discharged from the differential mobility classifier 5 and supplied through the particle supply pipe 37 into the outer vessel 34 deposit on the conductive filter 38 held in the inner container 36. The charged particles deposited on the conductive filter 38 discharge and produce a weak current. The weak current produced in the conductive filter 38 flows through the conductive rod 39 and the receiving part 41 into the preamplifier 42. The preamplifier 42 converts the weak current into a corresponding voltage and amplifies the voltage. The voltage thus amplified by the preamplifier 42 is applied through the double-shielded wire 43 to the electrometer 44. The electrometer 44 indicates the current, i.e., the amount of charge of the charged particles. The relation between the current i indicated by the electrometer 44, and the particle concentration $N_g$, i.e., the number of the charged particles contained in unit volume of the carrier gas is expressed by Expression (1):

$$N_g = i/(n \cdot \eta \cdot e \cdot q), \tag{1}$$

where n is the amount of charge of the charged particles, $\eta$ is charging efficiency, e is elementary electric charge ($1.6 \times 10^{-19}$ C) and q is the flow rate of the carrier gas.

The concentration $N_1$ of particles suspended in a liquid to be analyzed can be obtained by multiplying the concentration $N_g$ calculated by using Expression (1) by the ratio of the flow rate $Q_g$ of the carrier gas to the flow rate $Q_1$ of the liquid suspending the particles. Namely, the concentration $N_1$ is calculated by Expression (2):

$$N_1 = N_g \cdot (Q_g/Q_1). \tag{2}$$

Thus, the concentrations (the number of particles per unit volume) of the groups of the particles of specific particle sizes classified by the differential mobility classifier 5 in the liquid to be analyzed can be determined. The particle size of each group of the particles to be classified by the differential mobility classifier 5 can be determined by properly determining the voltage to be applied to the center rod 27. The particle sizes of the charged particles to be classified by the differential mobility classifier 5 are changed successively and the particle sizes of the groups of the charged particles are determined successively, so that a particle size distribution (the relation between the particle size and the number of charged particles per unit volume) of the charged particles suspended in the liquid to be analyzed can be determined.

If the charged fine liquid droplets collide against the inner surface of the cylindrical vessel 14 of the atomizer 13 included in the fine liquid droplet producing device 3, the fine liquid droplets are discharged, which causes an error in the number of the charged particles measured by the Faraday cup electrometer 6. Therefore, it is preferable to measure the amount of charge discharged from the fine liquid droplets collided against the inner surface of the cylindrical vessel 14, i.e., a current, by the ammeter 19 connected to the cylindrical vessel 14 of the atomizer 13 and to correct the measurement provided by the Faraday cup electrometer 6 by using the measured charge.

The fine liquid droplet producing device 3 atomizes the liquid to be analyzed, i.e., the liquid suspending particles, into the fine liquid droplets suspended in the carrier gas, the evaporator 4 evaporates the liquid parts of the fine liquid droplets to produce the aerosol of the carrier gas and the charged particles suspended in the carrier gas. Therefore, charged particles including nanoparticles can be suspended in the carrier gas without causing the aggregation of the charged particles. Therefore, the charged particles suspended in the carrier gas can be classified by particle size by the differential mobility classifier 5, and the respective concentrations of the classified groups of the charged particles can be measured by the Faraday cup electrometer 6. Thus, the particle size distribution of the particles including nanoparticles and suspended in the liquid can be accurately determined in a short time.

Although the liquid-suspended particle analyzer in the preferred embodiment of the present invention described above employs the liquid supply device including the sample container 1 and the fixed-displacement pump 2, any suitable liquid supply device, such as a syringe, may be used instead of the foregoing liquid supply device.

An optional suitable measuring instrument, such as an ion counter or a nuclear condensation counter, may be used instead of the Faraday cup electrometer 6 employed in the foregoing embodiment as a particle counter for counting the charged particles classified by particle size by the differential mobility classifier 5.

Although the foregoing embodiment analyzes the particles by counting the number of charged particles classified by particle size by the differential mobility classifier 5 by using the particle counter, i.e., the Faraday cup electrometer 6, a mass analyzer or a particle collector may be used instead of the particle counter; and the composition of the particles may be determined or the source of the particles may be identified by analyzing the compositions of the groups of the particles classified by particle size.

Although the invention has been described in its preferred embodiments with a certain degree of particularity, many changes and variations are obviously possible therein. It is therefore to be understood that the present invention may be practiced otherwise than as specifically described herein without departing from the scope and spirit thereof.

What is claimed is:

1. A liquid-suspended particle analyzer for analyzing particles suspended in a liquid, comprising:

a liquid supply device that supplies a liquid to be analyzed;

a fine liquid droplet producing device, including an electrosprayer and an atomizer, that produces fine liquid droplets suspended in a carrier gas supplied to the atomizer by atomizing the liquid supplied by the liquid supply device;

a radiation source provided within the atomizer for charging the charged fine liquid droplets produced by the electrosprayer in a Boltzmann equilibrium charted distribution;

an evaporator connected to an outlet of said atomizer that produces an aerosol of the carrier gas and particles suspended in the carrier gas by evaporating the liquid parts of the fine liquid droplets produced by the fine liquid droplet producing device;

a classifier that classifies the particles of the aerosol produced by the evaporator into particle groups by particle size; and a particle analyzer that analyzes the particle groups of the particles classified by particle size by the classifier.

2. The liquid-suspended particle analyzer according to claim 1, wherein the electrosprayer converts the liquid supplied by the liquid supply device into charged fine liquid droplets, and the atomizer suspends the charged fine liquid droplets produced by the electrosprayer in the carrier gas.

3. The liquid-suspended particle analyzer according to claim 2, wherein an ammeter is connected to the atomizer to measure a quantity of charge discharged from the fine liquid droplets collided against an inner wall of the atomizer.

4. The liquid-suspended particle analyzer according to claim 1, wherein the classifier is a differential mobility classifier adapted to classify the particles of the aerosol produced by the evaporator according to mobility.

5. The liquid-suspended particle analyzer according to claim 1, wherein the particle analyzer is a particle counter adapted to count respective numbers of the particles of the particle groups classified by the classifier.

6. The liquid-suspended particle analyzer according to claim 5, wherein the particle counter is one selected from a group consisting of a Faraday cup electrometer, an ion counter arid a nuclear condensation counter.

7. A liquid-suspended particle analyzing method of analyzing particles suspended in a liquid, said method comprising the steps of:
producing fine liquid droplets suspended in a carrier gas by atomizing a liquid to be analyzed;
providing a radiation source for charging the fine liquid droplets according to Boltzmann equilibrium charged distribution;
producing an aerosol of the carrier gas and particles suspended in the carrier gas by evaporating liquid parts of the fine liquid;
classifying the particles of the aerosol into particle groups by particle size; and
analyzing the particle groups of the particles classified by particle size.

8. The liquid-suspended particle analyzing method according to claim 7, wherein, in the step of analyzing the particles of the particle groups, respective numbers of the particles of the particle groups classified by particle size are counted so that a particle size distribution of the particles suspended in the liquid is determined on the basis of the counted numbers of the particles.

9. A liquid-suspended particle analyzer for analyzing particles suspended in a liquid, comprising:
a liquid supply device that supplies a liquid to be analyzed;
a fine liquid droplet producing device, including an electrosprayer and an atomizer, that produces fine liquid droplets suspended in a carrier gas supplied to the atomizer by atomizing the liquid supplied by the liquid supply device;
an evaporator connected to an outlet of said atomizer that produces an aerosol of the carrier gas and particles suspended in the carrier gas by evaporating the liquid parts of the fine liquid droplets produced by the fine liquid droplet producing device;
a classifier that classifies the particles of the aerosol produced by the evaporator into particle groups by particle size; and
a particle analyzer that analyzes the particle groups of the particles classified by particle size by the classifier;
wherein said evaporator includes a heater for evaporating liquid parts of said fine liquid droplets and a cooling device for condensing evaporated liquid for recovery.

10. A liquid-suspended particle analyzer for analyzing particles suspended in a liquid, comprising:
a liquid supply device that supplies a liquid to be analyzed;
a fine liquid droplet producing device, including an electrosprayer and an atomizer, that produces fine liquid droplets suspended in a carrier gas supplied to the atomizer by atomizing the liquid supplied by the liquid supply device;
a radiation source provided within the atomizer for charging the charged fine liquid droplets produced by the electrosprayer in a Boltzmann equilibrium charged distribution;
an evaporator connected to an outlet of said atomizer that produces an aerosol of the carrier gas and particles suspended in the carrier gas by evaporating the liquid parts of the fine liquid droplets produced by the fine liquid droplet producing device;
a classifier that classifies the particles of the aerosol produced by the evaporator into particle groups by particle size; and
a particle analyzer that analyzes the particle groups of the particles classified by particle size by the classifier;
wherein an ammeter is connected to the atomizer to measure a quantity of charge discharged from the fine liquid droplets collided against an inner wall of the atomizer.

* * * * *